United States Patent
Döring et al.

(10) Patent No.: US 10,383,696 B2
(45) Date of Patent: Aug. 20, 2019

(54) MEDICAL STERILE PACKAGING UNIT

(71) Applicant: B. BRAUN AVITUM AG, Melsungen (DE)

(72) Inventors: Stefan Döring, Dresden (DE); Peter Wiegers, Stuttgart (DE)

(73) Assignee: B. Braun Avitum AG (DE)

( * ) Notice: Subject to any disclaimer, the term of this patent is extended or adjusted under 35 U.S.C. 154(b) by 153 days.

(21) Appl. No.: 15/419,188

(22) Filed: Jan. 30, 2017

(65) Prior Publication Data

US 2017/0224433 A1 Aug. 10, 2017

(30) Foreign Application Priority Data

Feb. 5, 2016 (DE) .......... 10 2016 102 089

(51) Int. Cl.
*A61M 1/16* (2006.01)
*A61M 1/34* (2006.01)
(Continued)

(52) U.S. Cl.
CPC .............. *A61B 50/33* (2016.02); *A61B 50/30* (2016.02); *A61M 1/16* (2013.01); *A61M 1/34* (2013.01); *A61M 1/367* (2013.01); *B65D 21/0233* (2013.01); *B65D 25/10* (2013.01); *B65D 71/063* (2013.01); *B65D 75/36* (2013.01); *B65D 77/003* (2013.01); *B65D 77/0446* (2013.01); *B65D 81/266* (2013.01); *A61B 50/22* (2016.02); *A61B 2050/0065* (2016.02);
(Continued)

(58) Field of Classification Search
CPC .. B65D 21/0233; B65D 25/10; B65D 71/063; B65D 75/36; B65D 77/003; B65D 77/0446; B65D 81/266; A61B 50/30; A61B 50/33; A61M 1/16; A61M 1/34; A61M 1/367
USPC .......................................... 206/205, 386–600
See application file for complete search history.

(56) References Cited

U.S. PATENT DOCUMENTS

| | | | |
|---|---|---|---|
| 2,888,164 A * | 5/1959 | Corwin .................. | B65D 71/50 206/160 |
| 3,272,371 A * | 9/1966 | Weiner ..................... | B65D 1/36 206/443 |

(Continued)

FOREIGN PATENT DOCUMENTS

| | | |
|---|---|---|
| CN | 1600382 A | 3/2005 |
| CN | 201043034 Y | 4/2008 |

(Continued)

OTHER PUBLICATIONS

German Search Report for German Application No. 10 2016 102 089.3, dated Nov. 2, 2016, with translation, 11 pages.

(Continued)

*Primary Examiner* — Chun Hoi Cheung
(74) *Attorney, Agent, or Firm* — RatnerPrestia

(57) ABSTRACT

A medical sterile packaging unit for a sterile-packaged medical product, in particular for a filter module, including a primary packaging with at least one sterile-packaged and hermetically sealed medical product inside it, at least one nestable tray, with a plurality of inserts for each of the medical products packaged in the primary packaging, and at least one sleeve which wraps around the at least one tray with the primary-packaged medical products contained in it.

12 Claims, 1 Drawing Sheet

(51) Int. Cl.

| | |
|---|---|
| *A61M 1/36* | (2006.01) |
| *A61B 50/00* | (2016.01) |
| *A61B 50/22* | (2016.01) |
| *A61B 50/30* | (2016.01) |
| *A61B 50/31* | (2016.01) |
| *A61B 50/33* | (2016.01) |
| *B65D 21/02* | (2006.01) |
| *B65D 25/10* | (2006.01) |
| *B65D 71/06* | (2006.01) |
| *B65D 75/36* | (2006.01) |
| *B65D 77/00* | (2006.01) |
| *B65D 77/04* | (2006.01) |
| *B65D 81/26* | (2006.01) |

(52) U.S. Cl.
CPC ............... *A61B 2050/3006* (2016.02); *A61B 2050/3007* (2016.02); *A61B 2050/3008* (2016.02); *A61B 2050/3009* (2016.02); *A61B 2050/311* (2016.02); *A61M 2209/06* (2013.01)

(56) References Cited

U.S. PATENT DOCUMENTS

| | | | | |
|---|---|---|---|---|
| 3,322,266 A | * | 5/1967 | Lontz | ............... B01D 61/30 |
| | | | | 206/205 |
| 3,463,378 A | * | 8/1969 | Van Daalen | ............. B65D 1/48 |
| | | | | 206/512 |
| 4,529,088 A | * | 7/1985 | Quong | ................... B65D 85/34 |
| | | | | 206/509 |
| 4,832,208 A | * | 5/1989 | Finnegan | ................ A47F 5/005 |
| | | | | 206/564 |
| 5,573,117 A | * | 11/1996 | Adams | ............... B65D 77/0413 |
| | | | | 206/449 |
| 7,124,890 B2 | | 10/2006 | McLeod et al. | |
| 2003/0213718 A1 | | 11/2003 | Ducharme et al. | |
| 2005/0063859 A1 | * | 3/2005 | Masuda | ................ A61L 2/0035 |
| | | | | 422/44 |
| 2010/0015347 A1 | | 1/2010 | De Kock | |
| 2011/0284411 A1 | * | 11/2011 | Delbrouck | ............ B62B 5/0083 |
| | | | | 206/427 |
| 2014/0262883 A1 | * | 9/2014 | Devouassoux | ....... A61M 5/002 |
| | | | | 206/364 |
| 2014/0374414 A1 | | 12/2014 | Lanier et al. | |

FOREIGN PATENT DOCUMENTS

| | | |
|---|---|---|
| CN | 203127507 U | 8/2013 |
| CN | 103796926 A | 5/2014 |
| DE | 1871158 U | 4/1963 |
| DE | 9107610 U1 | 9/1991 |
| DE | 202004003964 U1 | 6/2004 |
| DE | 102007036734 A1 | 2/2009 |
| FR | 2195217 A5 | 3/1974 |
| GB | 2374413 A | 10/2002 |
| GB | 2525694 A | 11/2015 |
| JP | 2011006082 A | 1/2011 |
| WO | 02083311 A2 | 10/2002 |

OTHER PUBLICATIONS

European Search Report for European Application No. 17153392.0-1659, dated Jun. 21, 2017, 8 Pages.

Chinese Office Action for Chinese Application No. 201710066244.3, dated May 17, 2019, with translation, 17 pages.

* cited by examiner

MEDICAL STERILE PACKAGING UNIT

CROSS REFERENCE TO RELATED APPLICATIONS

This application claims priority to German application DE 10 2016 102 089.3 filed Feb. 5, 2016, the contents of such application being incorporated by reference herein.

FIELD OF THE INVENTION

The invention relates to a medical sterile packaging unit for a sterile-packaged medical product, in particular for a filter module/a dialyzer (filter cartridge, filter for a blood treatment machine, etc.).

BACKGROUND OF THE INVENTION

In the manufacture of sterile medical products, in particular filter modules/dialyzers, care must be taken to ensure that the product remains sterile until used on a patient or applied as part of a treatment. For this purpose, it must be ensured that either the sterile barrier is applied to the product itself or that the packaging forms a sterile barrier to the environment which remains intact for the shelf-life time shown on the product, assuming realistic storage conditions.

In terms of their external shape, filter modules/dialyzers are designed solely from the point of the demands of production and application technology. Obviously this shape creates particular demands in terms of the packaging of the filter module/dialyzer. An especially problematic feature of the packaging are the standardized, protruding and sharp-edged connectors on the filter module/dialyzer, edges on the filter module/dialyzer and protection caps on the filter module/dialyzer.

Known packagings for medical products, in particular for filter modules/dialyzers, primarily consist of a bag made of plastic or aluminium tube or a seal edge bag (as primary packaging), also a tray made of plastic, cardboard or molded pulp and if necessary an external box (as secondary packaging). The tray in particular has generally a shape, which substantially corresponds to the shape of the product packaged in the primary packaging, resulting in a kind of form fit which aims to achieve positionally stable packaging.

Some medical products, in particular filter modules/dialyzers, have to be sterilized in oxygen-free conditions where applicable. This means that at the time of sterilization, the inside of the primary packaging has to be (absolutely) oxygen-free. This is normally realized by absorption of the oxygen with a suitable medium, a so-called getter. The medium material can be iron powder or a polymer, for example. The absorber can be added to the primary packaging as a so-called sachet or integrated in the structure of the packaging material (foil).

It is a significant disadvantage that the binding of molecular oxygen in the closed system of the primary packaging results in a volume reduction or negative pressure (in an environment which does not change shape). Known packaging systems are not dimensionally stable, so that after closure of the packaging, their volume is uncontrollably reduced corresponding to the oxygen binding. Such a volume reduction of the primary packaging allows relative movements between the packaged filter modules/dialyzers among each other inside the secondary packaging as well as between the packaged filter modules/dialyzers and the secondary packaging, wherein this relative movements can in turn result in damage to the sterile barrier. Conventional trays and external boxes cannot respond to such a change or reduction in volume since they are rigid.

Another disadvantage of known packaging systems is that they are fixed in terms of the number of products they contain. This is all the more significant in view of the fact that filter modules/dialyzers are put on the market in different sizes so as to meet the need for differing volumes of blood of individual patients. Generally speaking it tends to be the diameter rather than the length of the component that is varied (for reasons relating to production and logistics). As the membrane surface is enlarged, the diameter of the component increases. Generally speaking, trays and external boxes with specific diameters are then required.

Finally, certain medical products such as filter modules/dialyzers are stored separately from the treatment room in day-to-day hospital routine. Hospital staff therefore regularly have to transport the products from a depot to a treatment room. Up to now, no aids have existed for this purpose. Staff have had to rely on their own solutions to carry out this transportation. At times this has resulted in the use of ineffective methods of transport which have often impaired the sterile barrier in the packaging.

SUMMARY OF THE INVENTION

Based on the above description of the state of the art, an object of the present invention is to eliminate the above-mentioned disadvantages, in particular to provide a sterile packaging unit for medical products, preferably filter modules/dialyzers, with which it is possible to minimize or preferably prevent damages to the sterile barrier resulting from relative movements between packagings as is made possible by uncontrolled volume reduction. The packaging itself should preferably be insensitive to volume reduction as well as being low-cost and dimensionally stable. Finally, the sterile packaging unit preferably has to be adaptable to the size of the medical products packaged inside it and has to be largely variable with regard to the number of medical products packaged. Furthermore, manufacturing costs and packaging effort are preferably to be minimized, and also product protection is to be ensured, including when the product is outside the external packaging.

According to aspects of the invention, this object is achieved with a (medical) sterile packaging unit for a sterile-packaged medical product (of a sterile-packaged medical product), preferably a filter module and in particular a dialyzer, comprising a primary packaging, the medical product packaged in a sterile and hermetically sealed manner in the primary packaging, at least one nestable tray, for example in the form of a crate, with a number of inserts, preferably several inserts, one for each of the medical products packaged in the primary packaging, and a sleeve or strapping element which wraps around at least one tray containing the primary packaged medical products. The medical product can in particular be a dialyzer or a filter module. This can in particular comprise an essentially cylindrical central section and a filter module/dialyzer connection formed at the end of the central section.

The background of the invention is to provide a nestable secondary packaging for medical products which are sterile-packaged (primary packaged) in any way, in particular filter modules or dialyzers, with the design of the nestable secondary packaging enabling it to serve both as a tray and as an external box. In addition to reducing packaging effort and cost, convenient handling of the components is also enabled for the user: the trays can be stored in shelves without strapping, for example, and they provide the products with comprehensive protection both on the shelf and during transportation. As a result, storage damage is largely avoided. In addition, the trays can be used as a transport facility by the user, for example when carrying the products from the depot to the place of therapy. An additional advantage is that the tray, as a single element, performs a number of functions for which several elements or units are required in the state of the art. This is because it performs the function of both a tray and of secondary packaging. By stacking a smaller or greater number of trays, it is possible to combine a smaller or greater number of filter modules/dialyzers in a single packaging unit (previously in a box with a fixed number of packaged units) and to deliver them as a single packaging unit. The tray acts as a secure transportation aid for a manageable number of filter modules/dialyzers. Packaging waste can also be saved as a result of the invention. Conventional packaging systems generally involve the packaged medical products being secured in a box with intermediate layers or trays. Once emptied, it is necessary to dispose of all the boxes, intermediate layers and trays. The packaging system according to aspects of the invention eliminates the waste volume of the box, since here it is not required. Finally, the tray makes it simpler to handle filter modules/dialyzers stored on it, especially once they have been unpacked. The tray is designed (in particular with regard to its torsional stiffness) so as to serve as a kind of support base for the unpacked filter modules/dialyzers on which the filter modules/dialyzers can be stored for free removal.

Preferred embodiments of the invention are claimed in the dependent claims and are explained below.

The primary packaging can in particular exhibit a getter to bind molecular oxygen in the primary packaging so that it is subsequently possible to carry out sterilization with radiation (gamma).

The primary packaging is preferably a blister packaging, in particular a hard-hard or a hard-soft blister. It can exhibit a plastic molded part forming an insert for a medical product as its lower section and an insert for a closing as its upper section, wherein the upper section is fixed onto the lower section so as to be hermetically sealed (welded, bonded, etc.).

The sleeve is preferably made of paper, packing paper, cardboard, foil, plastic foil or a fabric material. In particular, it can be elastic. In this way, elastic deformation enables the sleeve to follow the changes in dimension of a tray or of the trays around which it is wrapped together with the primary packaged medical products inserted in them (lengthening/shortening).

The tray preferably has a base, and side walls arranged around this base. The plurality of inserts take the form of recesses, waves, etc., for example, configured in or on the base or by the base. In particular, the base can be configured to be wave-shaped with recesses and protrusions in such a way that the latter are formed both on the upper side and the lower side of the base.

In a preferred embodiment, the side walls of the tray are arranged or configured conical. In this way, the side walls on the upper side of the tray are spaced further apart from each other than on the lower side of the tray and/or on the base. Conventional trays with external boxes cannot respond to a reduction in volume since they are rigid. The above-mentioned embodiment is able to overcome this disadvantage since the trays can engage with each other due to their conical shape and adapt to a volume reduction, e.g. of the primary packagings inserted in them, for example due to the binding of molecular oxygen in the primary packaging. The trays can be inserted into each other in such a way that it is possible to use only one universal tray to hold differing primary packagings with different external diameters. One can also say that the interlocked stacking of trays enables an adaptation of the packaging system to the product sizes. To put it differently, stacked trays can be positioned relative to one another vertically in such a way that it is possible to allow for volume changes within the primary packagings, for example.

Especially good protection of the primary packaged medical products can be achieved if the side walls extend above the primary packaged medical products arranged in the inserts of the tray. Another way of achieving this is for the tray to comprise corner sections, in particular stabilizing corner sections, which protrude beyond the side walls.

Particularly good adaptability of the sterile packaging unit can be achieved by arranging a plurality of trays on top of each other, with the primary packaged medical products inserted in them, wherein the base of a tray rests on the primary packaged medical products in the tray below it and/or the conically arranged side walls of a tray rest on the conically arranged side walls of the tray below it.

In particular, the medical product can be a filter module/dialyzer sterile-packaged in primary packaging with a substantially cylindrical central section and a filter module/dialyzer connection formed at the end of the central section, preferably a filter module/dialyzer connection formed at each end of the central section. The primary packaging can in particular be blister packaging with a plastic molded part forming an insert for the filter module/dialyzer as the lower section and an upper foil combined with the latter to form an insertion space for the filter module/dialyzer. The upper foil can be fixed onto the lower section so as to be hermetically sealed and fix the filter module/dialyzer at least partially with form fit, in particular with respect to the lower section or between itself and the lower section. The upper foil can in particular fit up against at least the central section of the filter module/dialyzer. Between the lower section and the upper foil there is then only a small amount of air and therefore molecular oxygen, which is advantageous for the sterilization of the filter module/dialyzer packaged in the primary packaging. In the event of sterilization with radiation/gamma radiation, for the purpose of which molecular oxygen has to be removed from the closed and sealed packaging, any reduction in volume as a result of sterilization will therefore advantageously be slight as a result.

The primary packaging is preferably designed in such a way that the medical product, in particular the filter module/dialyzer, is securely held and fixed in position inside it. According to an embodiment, an area inside the packaging can be defined at which the packaging, in particular the molded part, can deform as a result of a volume reduction without impairing the overall stability and basic shape of the packaging. Without impairing the basic shape of the packaging in this sense means that certain external areas of the packaging, with which it rests on other primary packagings or an external packaging, for example, are not subject to deformation. Interior sections of the packaging are likewise substantially resistant to deformation, in particular the molded part, with which or on which the filter module/dialyzer is held, positioned or supported.

A particular feature of the invention is that the lower section can be designed in such a way that it securely holds the medical product, in particular the filter module/dialyzer. The lower section is preferably configured in the manner of a tray which has a recess for the medical product, the height of which is significantly less than the dimensions of the medical product transversely to its axial direction, however. The depth of the insert configured in the lower section is preferably less than half the diameter of the medical product, especially preferably less than a third of the diameter of the medical product, even more preferably less than a quarter of the diameter of the medical product. This is a simple way to ensure that the medical product is largely enveloped by the upper foil and fixed in position by the latter. Furthermore, the lower section can be designed in such a way that closing of the filter module/dialyzer connections by the upper foil is prevented or not possible. In the event of radiation (gamma) sterilization, these connections must necessarily remain unobstructed so as to permit movement of oxygen molecules out of the fibre bundle of the filter module/dialyzer. In particular, the upper foil can fit (tightly) against the cylindrical central section of the filter module/dialyzer and not come into contact with the filter module/dialyzer connections formed at each end of the central section of the filter module/dialyzer. The upper foil is preferably shrink foil.

The rigid lower section of the blister combination can exhibit an edge. The upper foil can be sealed on the preferably continuously peripheral edge of the lower section. The edge can in particular interlock with the tray and fit against the latter's side walls, thereby limiting or preventing relative movement between the primary packaging and the tray.

The lower section forms a connection insert which is widened with respect to the external contour of the filter module/dialyzer, in particular with respect to the filter module/dialyzer connections, preferably at each end of the central section of the filter module/dialyzer. It is possible for the filter module/dialyzer connections to be held in this insert so that the latter are, advantageously, not closed by either the lower section or the upper foil, while also remaining open in the respective connection insert and fluidically connected to the insertion space, in particular to the connection insert volume.

The tray is preferably configured in such a way that there is a form fit with the primary packaged medical product in the axial direction and/or in the tangential direction. The inserts can be made available in the base in the form of recesses, preferably part-cylindrical recesses. In each case, a primary packaging can be or is inserted so as to interlock with a recess.

In summary it can be said that the invention describes a possibility of packaging sterile-packaged medical products, in particular filter modules/dialyzers of differing external measurements (diameters), in a universal tray. The trays are inserted into one another according to size and for shipping purposes simply strapped with a sleeve, for example made of paper. In addition, the tray serves the user for the purpose of storage and transport stabilization.

The invention can be used to achieve the following advantages, among others:
  it saves the use of size-specific interim layers (trays) and external boxes, thereby reducing manufacturing costs,
  it enables improved automation (handling), which leads to a reduction in manufacturing costs,
  it permits a large number of medical products to be packaged in the box, therefore resulting in a reduction in logistics costs,
  it limits diverse relative movement between the primary packaging and the external packaging with a yielding plug connection between the trays,
  it allows variation of the number of filter modules/dialyzers in the packaging unit,
  it enables simplified and secure transport and storage of the filter modules/dialyzers in the hospital and
  it reduces packaging waste.

BRIEF DESCRIPTION OF THE DRAWING

The invention is best understood from the following detailed description when read in connection with the accompanying drawing. Included in the drawing are the following figures.

DETAILED DESCRIPTION OF PREFERRED EMBODIMENTS

The expression "dialyzer" as used below is to be understood in such a way as to include other types of filter module, too.

Figure 1:
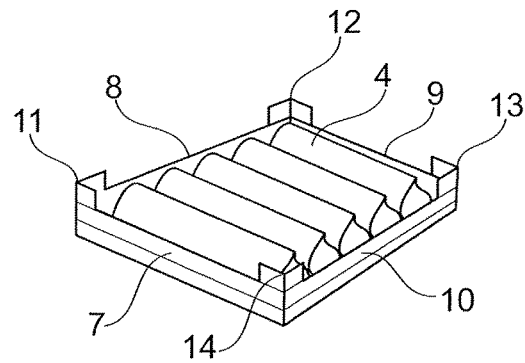
FIG. 1 shows a schematic perspective of a tray of a sterile packaging unit.
Figure 2:
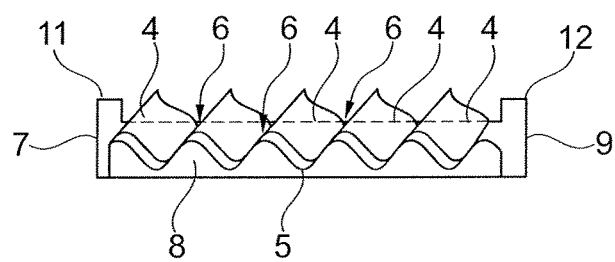
FIG. 2 shows the tray of FIG. 1 in cross-section transversely to the axial direction.
Figure 4:
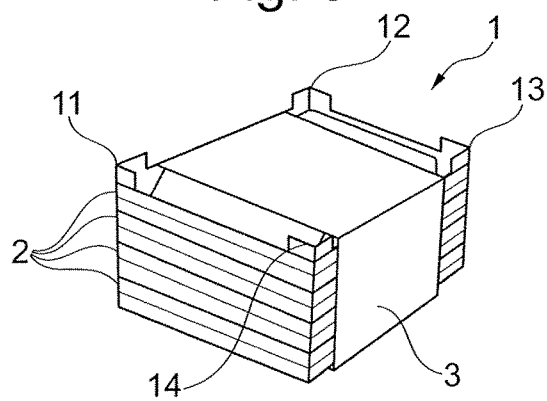
FIG. 4 shows a perspective view of a sterile packaging unit in a second embodiment with the trays shown in FIGS. 1 and 2.

FIG. 4 shows a sterile packaging unit 1 with four trays 2 which are stacked on top of each other vertically and which are enveloped and held together by a shared sleeve 3. The sleeve 3 envelopes the trays 2 (essentially) fully, thereby forming the secondary packaging, so to speak. One of the trays 2 is shown in FIGS. 1 and 2. It preferably contains five dialyzer primary packagings 4, each consisting of primary packagings respectively containing one sterile-packaged dialyzer as a medical product respectively (not shown in the figures).

Each tray 2 comprises a base 5. The latter is preferably wave-like in configuration so that its upper side forms inserts 6 for the primary packaged dialyzers. The base 5 is surrounded by side walls 7, 8, 9, 10 which are connected to each other with corner sections 11, 12, 13, 14, thereby forming a frame. FIG. 2 in particular shows that the corner sections 11, 12, 13, 14 are higher than the primary packaged products 4 inserted in the tray 2. This creates a stackable dialyzer crate, so to speak.

Figure 3:
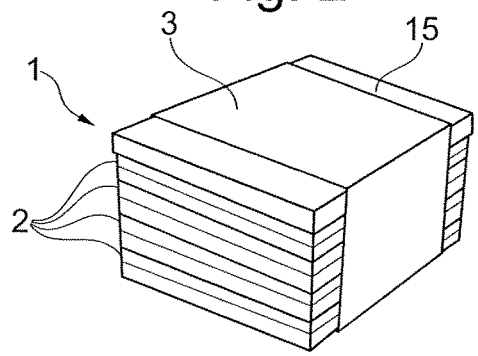
FIG. 3 shows a perspective view of a sterile packaging unit in a first embodiment.

In the embodiment shown in FIG. 3, the upper (uppermost) tray 2 of the tray stack has a lid 15 positioned on it which covers the primary packaged dialyzers and which is likewise additionally enveloped by the sleeve 3. FIGS. 3 and 4 show the sterile packaging unit 1 in a packaged state with the sleeve 3 ready for shipping. FIGS. 1 and 2 show the sterile packaging unit 1 in a state with the sleeve 3 removed, for example for storage on a user's premises and for transport from a storage depot to an application.

The invention claimed is:

1. A medical sterile packaging unit with a sterile-packaged medical product, the medical sterile packaging unit comprising:
  a plurality of primary packagings, each primary packaging containing a sterile-packaged medical product hermetically sealed within the primary packaging;
  a plurality of nestable trays, each nestable tray including raised corner sections that project above the plurality of packagings and an insert for each of the medical products packaged in the primary packagings; and
  a lid for placement over the raised corner sections of one of the nestable trays, wherein:

each of the plurality of nestable trays comprises a base and side walls arranged around the base in a unitary construction, with one of the side walls arranged on each side of the base, the side walls of each tray are conical such that opposing side walls are tapered outwardly toward an upper side of the tray such that the opposing side walls are spaced further apart at the upper side of the tray than at a lower side of the tray and/or the base;

at least one sleeve that wraps around the plurality of nestable trays with the plurality of primary packagings;

the inserts are formed in, on, or by the base; and the base comprises a wave-shape defining recesses and protrusions formed on both an upper side of the base and on a lower side of the base.

2. The medical sterile packaging unit of claim 1, wherein the medical product is a filter module.

3. The medical sterile packaging unit of claim 1, wherein each of the plurality of primary packagings includes at least one getter to bind molecular oxygen in the primary packaging.

4. The medical sterile packaging unit of claim 1, wherein each of the plurality of primary packagings is a blister packaging including a plastic molded part forming an insert for a respective medical product as a lower section and an upper section that closes the insert, wherein the upper section is fixed onto the lower section so as to be hermetically sealed.

5. The medical sterile packaging unit of claim 1, wherein the at least one sleeve is paper, packing paper, cardboard, foil, plastic foil or a fabric material.

6. The medical sterile packaging unit of claim 1, wherein the at least one sleeve is elastic and can follow changes in size of the plurality of nestable trays with the plurality of primary packagings.

7. The medical sterile packaging unit of claim 1, wherein the side walls extend above the primary packaging containing the sterile-packaged medical product arranged in the inserts of the tray.

8. The medical sterile packaging unit of claim 1, wherein the corner sections are stabilizing corner sections.

9. The medical sterile packaging unit of claim 1, wherein the plurality of nestable trays are arranged on top of each other, with the primary packaging containing the sterile-packaged medical product arranged in the inserts of the trays, wherein the base of a first of the plurality of nestable trays rests on the primary packaging containing the sterile-packaged medical product arranged in a second of the plurality of nestable trays positioned below the first of the plurality of nestable trays.

10. The medical sterile packaging unit of claim 1, wherein the plurality of nestable trays are arranged on top of each other, with the primary packaging containing the sterile-packaged medical product arranged in the inserts of the trays, wherein the conical side walls of a first of the plurality of nestable trays rest on the conical side walls of a second of the plurality of nestable trays positioned below the first of the plurality of nestable trays.

11. The medical sterile packaging unit of claim 1, wherein the medical product is a filter module, wherein the filter module comprises a substantially cylindrical central section and a filter module connection formed at an end of the central section.

12. A medical sterile packaging unit with a sterile-packaged medical product, the medical sterile packaging unit comprising:

a plurality of primary packagings, each primary packaging containing a sterile-packaged medical product sealed within the primary packaging;

a plurality of nestable trays in a stack, each nestable tray including raised corner sections that project above the plurality of packagings and a base comprising a wave-shape that defines recesses and protrusions formed on both an upper side of the base and on a lower side of the base; and a lid placed over the raised corner sections of one of the nestable trays, wherein:

the plurality of primary packagings are inserted into the recesses;

each of the plurality of nestable trays comprises side walls arranged around the base in a unitary construction with one of the side walls arranged on each side of the base, and the side walls of each nestable tray are tapered outwardly toward an upper side of the tray such that opposing side walls are spaced further apart at the upper side of the tray than at a lower side of the tray.

* * * * *